Figure 1:
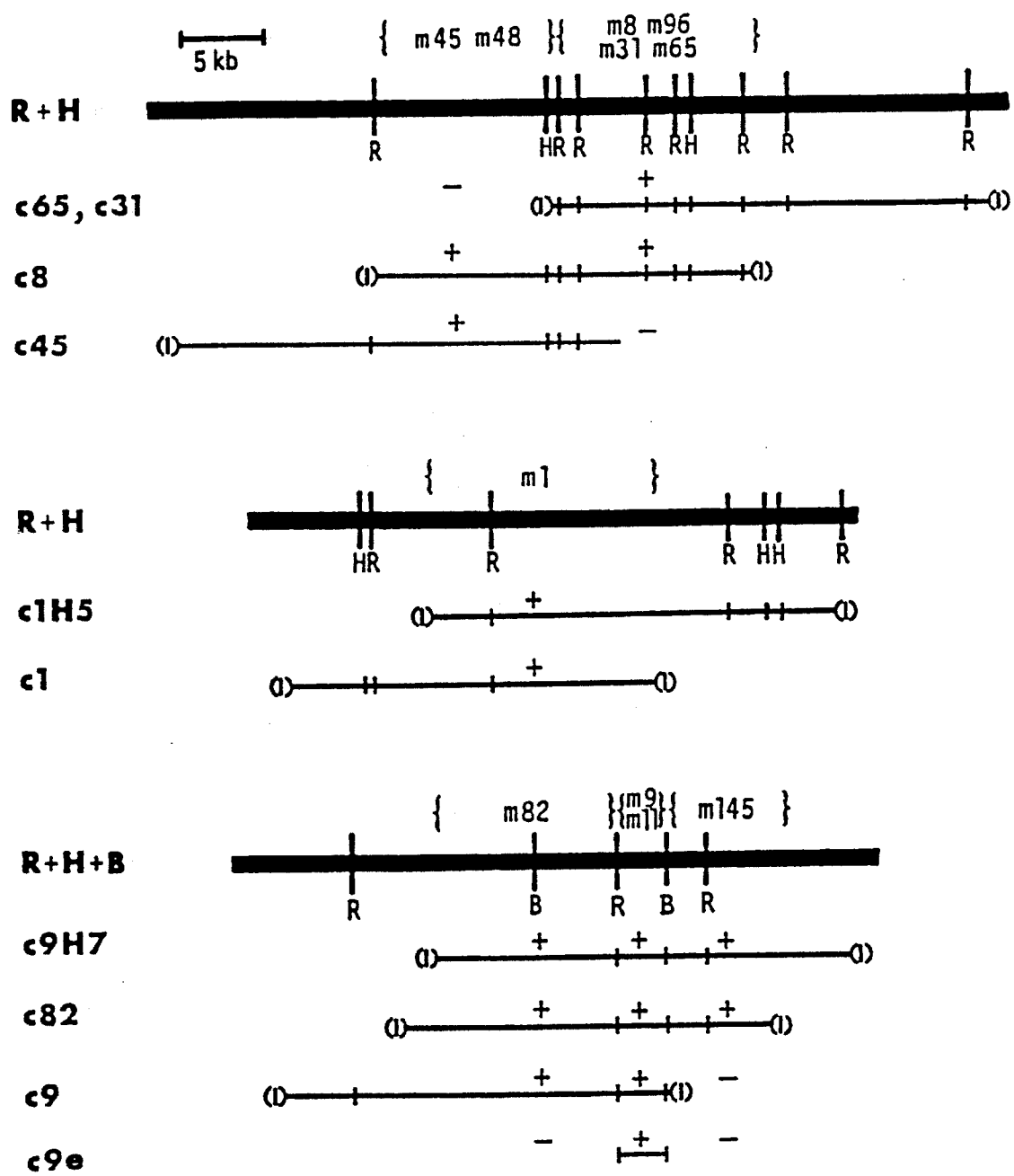

United States Patent [19]

Pollock et al.

[11] Patent Number: 5,472,870
[45] Date of Patent: Dec. 5, 1995

[54] BIOLOGICALLY PURE CULTURE OF A STRAIN OF XANTHOMONAS COMPESTRIS ATCC 55429

[75] Inventors: Thomas J. Pollock; Linda Thorne, both of San Diego, Calif.

[73] Assignees: Shin-Etsu Chemical Co., Ltd., Tokyo, Japan; Shin-Etsu Bio, Inc., San Diego, Calif.

[21] Appl. No.: 826,095

[22] Filed: Jan. 27, 1992

Related U.S. Application Data

[62] Division of Ser. No. 479,196, Feb. 13, 1990, Pat. No. 5,194,386, which is a continuation of Ser. No. 38,302, Apr. 14, 1987, abandoned.

[51] Int. Cl.⁶ .............................. C12N 1/12; C12N 1/20; C12P 19/06
[52] U.S. Cl. .................. 435/252.1; 435/910; 435/104
[58] Field of Search ....................... 435/252.1, 910, 435/104

[56] References Cited

U.S. PATENT DOCUMENTS

| | | | |
|---|---|---|---|
| 4,136,177 | 1/1979 | Lin et al. | 514/478 |
| 4,245,046 | 11/1981 | Demain et al. | 435/104 |
| 4,296,203 | 10/1981 | Werkau | 435/104 |
| 4,418,145 | 11/1983 | Weisrock et al. | 435/910 |
| 4,717,663 | 1/1988 | Minoshima et al. | 435/104 |

*Primary Examiner*—Marian C. Knode
*Assistant Examiner*—Mike Meller
*Attorney, Agent, or Firm*—McAulay Fisher Nissen Goldberg & Kiel

[57] ABSTRACT

A method of increasing xanthan gum production, comprising culturing a *Xanthomonas campestris* strain having a xanthan-increasing modification in a culture medium, wherein the modification is selected from the group consisting of (1) a mutation causing rifampicin-resistance; (2) a mutation causing bacitracin-resistance; or (3) exogenous genetic information controlling the synthesis of xanthan; and separating xanthan from the culture medium, is provided along with specific DNA sequences and *Xanthomonas campestris* strains showing increased xanthan gum production. The strain is preferably ATCC 55429.

2 Claims, 2 Drawing Sheets

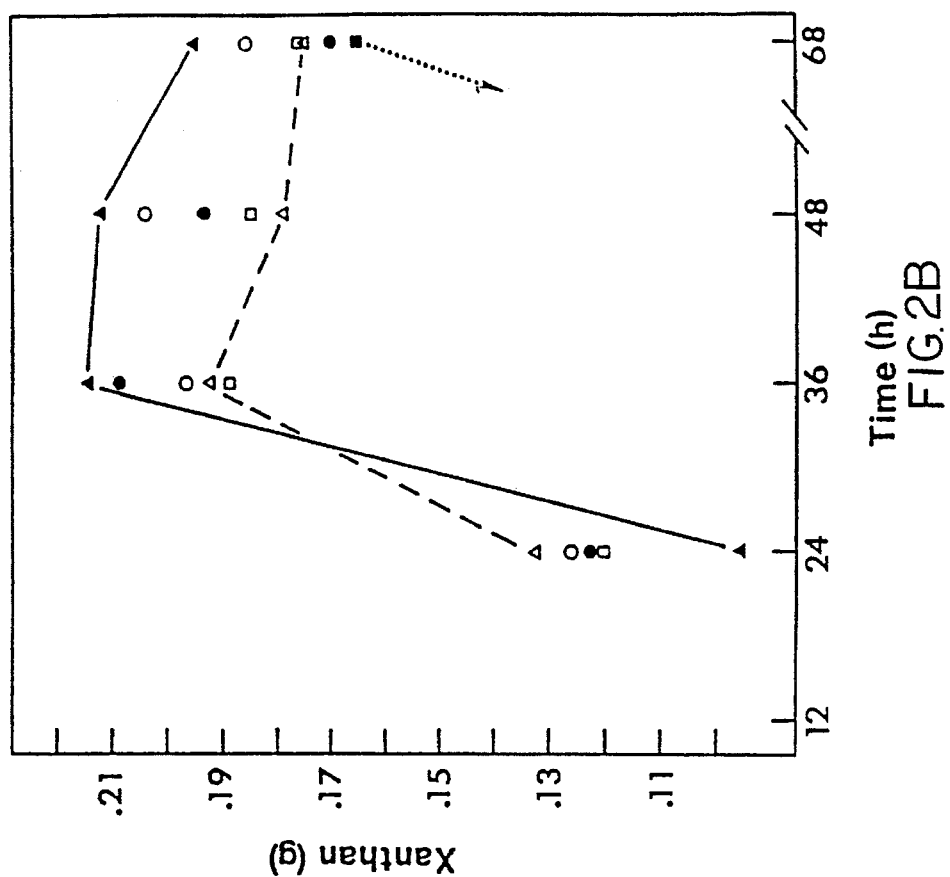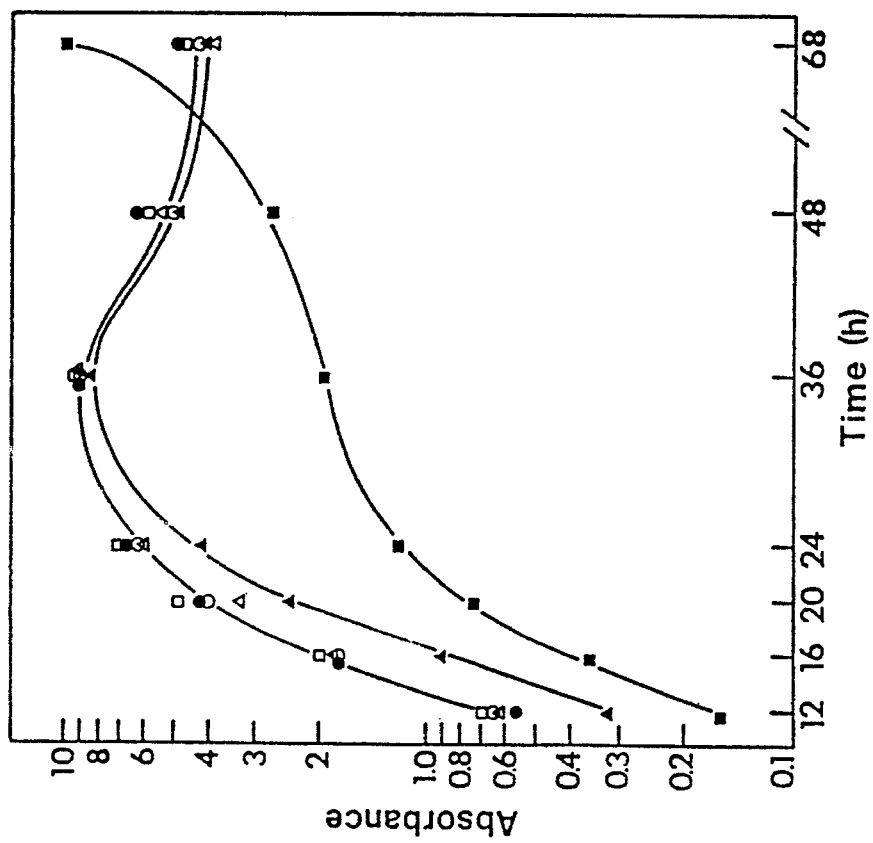

BIOLOGICALLY PURE CULTURE OF A STRAIN OF XANTHOMONAS COMPESTRIS ATCC 55429

This is a division of application Ser. No. 479,196, filed Feb. 13, 1990. U.S. Pat. No. 5,194,386, which in turn, is a continuation of application Ser. No. 038,302, filed Apr. 14, 1987, now abandoned.

BACKGROUND OF THE INVENTION

1. Field of the Invention

The present invention relates to the synthesis of xanthan gum by *Xanthomonas campestris* and particularly to methods for increasing synthesis by modifying the natural organism.

2. Background of the Invention

A number of microorganisms produce extracellular polysaccharides, also known as exopolysaccharides or EPS. The exopolysaccharide known as xanthan is produced by the bacterium *Xanthomonas campestris*. The strain *X campestris* pv *campestris* is a causal agent of black rot of crucifers.

Xanthan itself is useful as a specialty polymer for a growing number of commercial applications. The exploitation of xanthan as a commercial product results from a successful screening effort by the Northern Regional Research Center to find useful water-soluble polysaccharide products to replace existing gums from plant and algal sources. The NRRL discovered *X. campestris* NRRL B1459, a strain which produces a polymer that exhibits three desirable properties: (1) high viscosity at low concentrations; (2) pseudoplasticity; and (3) insensitivity to a wide range of temperature, pH, and electrolyte concentrations. Because of its special rheological properties, xanthan is used in food, cosmetics, pharmaceuticals, paper, paint, textiles, and adhesives and otherwise in the oil and gas industry.

In addition, the polymer is readily produced by fermentation from D-glucose. The synthesis of xanthan is believed to be similar to exopolysaccharide synthesis by other Gram-negative bacteria, such as species of Rhizobium, Pseudomonas, Klebsiella, and Escherichia. The synthetic pathway can be divided into three parts: (1) the uptake of simple sugars and their conversion to nucleotidal derivatives; (2) the assembly of pentasaccharide subunits attached to an isopentenyl pyrophosphate carrier; and (3) the polymerization of pentasaccharide repeat units and their secretion. By comparison to the more advanced molecular genetic understanding of colanic acid synthesis by *E. coli* or alginate synthesis by *P. aeruginosa*, little is known about the genes, enzymes, or mechanisms that control the synthesis of xanthan by *X. campestris*.

Accordingly, an increased understanding of the genetic control of xanthan production by *X. campestris* would be useful for improving the productivity of *X. campestris* for xanthan synthesis.

Description of Relevant Literature

A recent publication on the topic of molecular cloning of genes involved in the production of xanthan in Barrere et al., *Int. J. Biol. Macromol.* (1986) 8:372–374. A study showing that a mutation, which blocks exopolysaccharide synthesis and prevents nodulation of peas by *Rhizobium leguminosarum*, was corrected by cloned DNA from the phytopathogen Xanthomonas is described in Borthakur et al., *Mol. Gen. Genet.* (1986) 203:320–323. Production of xanthan using

*Xanthomonas campestris*, properties of xanthan, and commercial applications of xanthan are described in Rogovin et al., *J. Biochem. Microbiol. Technol. Eng.* (1961) 3:51– 63, and Kennedy et al., 1984, "Production, properties, and applications of xanthan", pp. 319–371 in M. E. Bushell (ed.), Progress in Industrial Microbiology, vol. 19, Elsevier, Amsterdam.

SUMMARY OF THE INVENTION

A method of increasing xanthan gum production is provided, which comprises culturing a *Xanthomonas campestris* strain having a xanthan-increasing modification in a culture medium, wherein said modification is selected from the group consisting of (1) a mutation causing rifampicin-resistance; (2) a mutation causing bacitracin-resistance; or (3) expressible exogenous genetic information controlling the synthesis of xanthan; and separating xanthan from the culture medium. A section of Xanthomonas chromosomal DNA containing genetic information controlling the synthesis of xanthan is identified, which allows use of numerous techniques for increasing xanthan production such as providing multiple copies to increase xanthan production by a dosage effect and providing an inducible promoter or other method of genetic control in order to de-couple xanthan production from constitutive protein synthesis. Mutations providing resistance to the indicated antibiotics can be obtained by standard techniques now that the specific antibiotic resistance factors capable of increasing xanthan production have been identified.

BRIEF DESCRIPTION OF THE DRAWINGS

The present invention will be better understood by reference to the following detailed description of specific embodiments when considered in combination with the enclosed drawings which form part of the specification, wherein:

FIG. 1 is a compilation of three physical maps for *X. campestris* DNA insertions in vector pRK311 showing complementation groups. The line marked "R/H" shows the order and position of restriction cleavage sites for EcoRI and HindIII enzymes deduced from the overlapping maps obtained for individual cloned inserts. Parentheses, (), at the end of the cloned maps indicate that it was not possible to distinguish between an end generated by cleavage within the cloned insert from restriction in the adjoining multiple cloning site. The tentative map positions for $Xgs^-$ mutations are indicated above the physical maps. Unordered loci are enclosed with braces, {}.

FIG. 2 is a graph showing time course of accumulation of xanthan by wild-type strain X59 carrying multiple copies of genetic information controlling the synthesis of xanthan. Recombinant plasmids containing inserts of cloned *X. campestris* DNA that restore xanthan synthesis are indicated by the following symbols: ●, X59; Δ, X59pRK311; ▲, X59c45;□, X59c9; ○, X59c1; ■, X59c31. Panel A shows optical density at various times of cell growth while Panel B shows xanthan accumulation. The upper curve in Panel A represents four cultures. In Panel B the solid line is for X59c45, the dashed line is for X59pRK311, and the dotted line is for X59c31.

DESCRIPTION OF SPECIFIC EMBODIMENTS

Investigations in the laboratories of the inventors have indicated that a number of modifications are available that are capable of increasing xanthan gum production from

*Xanthomonas campestris* strains. Three specific genetic modifications capable of increasing xanthan production are mutations causing rifampicin-resistance, mutations causing bacitracin-resistance, and the presence of exogenous genetic information controlling the synthesis of xanthan introduced into a *Xanthomonas campestris* strain.

The first two of these techniques, both of which involve utilization of a mutant strain having resistance to an antibiotic, can be carried out in a straightforward manner now that the relationship between antibiotic resistance and xanthan production has been determined.

Rifampicin is a member of the group of antibiotics known as rifamycins, produced by *Streptomyces mediterraniae*. They contain a napthalene ring system bridged between positions 2 and 5 by an aliphatic chain. Rifampicin is known to inhibit DNA-dependent RNA synthesis in prokaryotics, chloroplasts, and mitochondria. Inhibition is due to the formation of a stable complex between RNA polymerase and rifampicin. A description of rifampicin and other rifamycins is set forth in The Concise Encyclopedia of Biochemistry, Walter D. Gruyter, New York, 1983, p. 418.

Bacitracins are branched, cyclic peptides produced by various strains of *Bacillus licheniformis*. The most important of these peptides is bacitracin A, which contains a thiazoline structure synthesized from an N-terminal isoleucine and its neighboring cystine. The known motive action for bacitracins is by interference with murein synthesis. Murein is a cross-linked polysaccharide-peptide complex of indefinite size that forms a structural constituent of the inner wall layer of all bacteria. Murein consists of linear parallel chains of up to 20 alternating residues of $\beta$-1,4-linked residues of N-acetylglucosamine and N-acetylmuramic acid, extensively cross-linked by peptides.

Resistant mutants can be prepared by culturing a *Xanthomonas campestris* strain in a culture medium containing one or both of the indicated antibiotics. Antibiotic concentrations of from 1 μ/ml to 1000 μ/ml, preferably at least 5 μ/ml, more preferably at least 50 μ/ml, preferably no more than 500 μ/ml, more preferably no more than 250 μ/ml for rifampicin are useful as initial concentrations in the practice of the present invention. Antibiotic concentrations of from 100 μ/ml to 1000 μ/ml, preferably at least 200 μ/ml, more preferably at least 250 μ/ml, preferably no more than 500 μ/ml, more preferably no more than 400 μ/ml for bacitracin are useful as initial concentrations in the practice of the present invention. These concentrations can be adjusted upward or downward in response to observed conditions of growth and/or survival during cultivation. The remaining components of the culture medium are those normally used for Xanthomonas cultivation and include water, buffering agents such as ammonium phosphate and sodium nitrate, salts such as magnesium sulfate and calcium chloride, glucose sufficient to maintain growth, and trace minerals. Other components such as yeast extract, malt extract, peptone, and Amberex can be utilized if desired.

Selection can be made either for spontaneous mutations that survive growth in the selection media or mutations can be induced by a mutagen such as ultraviolet light or chemical mutagens. Examples of commonly used mutagens are X-rays, ultraviolet radiation at 260 nm, N-methyl-N'-nitro-N-nitrosoguanidine, methyl- and ethylmethanesulfonic acid, sodium nitrite, sodium bisulfite, hydroxylamine, nucleic acid base analogs such as 2-aminopurine and 5-bromouracil, and acridine dyes such as proflavin. Also useful are insertional mutations such as insertion sequences, Mu-1 phage, or transposons such as Tn5. A *Xanthomonas campestris* strain can be exposed to one or more of these mutatens either prior to or concurrently with growth of the strain on the selection medium.

Although not all mutants capable of resisting these two antibiotics show increased xanthan production, the proportion of mutants having increased xanthan production is sufficiently high to allow selection of strains having a xanthan-increasing modification as a result of genetic modification with relative ease. Selection for increased xanthan production can be carried out by measuring xanthan in the culture medium utilizing standard techniques, such as those exemplified in the Examples below. The selected hyperproducing strains can be either utilized as obtained or the genetic information occurring as a result of the mutation can be excised by known techniques of genetic engineering and inserted into other Xanthomonas strains for use in preparing xanthan by culturing techniques. Such genetically engineered strains containing a xanthan-increasing modification that originally arose in a different strain as a result of mutation to give either rifampicin- or bacitracin-resistance fall within the scope of the present invention. The techniques described below in both the general discussion and specific examples of genetic manipulation can be utilized to isolate the genetic information at the locus of the mutation and insert this genetic information into other strains of Xanthomonas.

The third specific technique described above for increasing xanthan production involves the use of exogenous genetic information controlling the synthesis of xanthan that has now been identified. Specific sections of Xanthomonas chromosomal DNA have been identified that control the synthesis of xanthan. FIG. 1 is a chromosome map providing restriction site information that is useful in identifying the proper sequences. Three deposits of genetic information have also been made with the American Type Culture Collection, Rockville, Md., U.S.A. The three deposits are *X. campestris* strains containing (individually) the three genetic segments identified in FIG. 1. These deposits have been accorded deposit numbers ATCC 67386, ATCC 67387 and ATCC 67388.

The genetic information from *X. campestris* can be utilized in many ways. Plasmids can be constructed containing the exogenous genetic information controlling the synthesis of xanthan, and genetic information can be introduced into an *X. campestris* host by utilizing a donor strain containing a plasmid with the desired genetic information in a triparental mating scheme to transfer the genetic information to *X. campestris*. Suitable vectors for conjugation include a variety of plasmids displaying a broad host range. For example, IncP-group plasmids, which include RK2 and its derivatives pRK290, pLAFR1, and pRK311, and IncQ-group plasmids, which include RSF1010 and its derivative pMMb24 can be utilized. References describing these plasmids include Ditta et al., *Plasmid* (1985) 13:149–153 (plasmids RK2, pRK290, and pRK311); Friedman et al., *Gene* (1982) 18:289–296 (pLAFRI); and Bagdasarian et al., *Gene* (1983) 26:273–282 (pMMb24). For example, *E. coli* donor cells containing the genetic information on a plasmid, *E. coli* HB101 helper cells containing plasmid pRK2013, and recipient *X. campestris* cells can be incubated to cause genetic information transfer by conjugation. Isolation of recombinant plasmids, for example by utilization of a marker present adjacent to the genetic information being transferred, can be followed by further purification and subsequent matings. With a purified member of the original gene library to raise the frequency of exconjugates containing the exogenous genetic information.

Individual genes encoding specific peptides or control factors utilized in the synthesis of xanthan can be isolated from the genetic information described above using standard techniques of recombinant DNA technology. Restriction endonucleases can be utilized to cleave the relatively large segment of genetic information containing xanthan genes into specific identifiable fragments. These fragments can be individually cloned and identified. Individual fragments can be inserted into new hosts to provide further *X. campestris* strains having increased xanthan production. Accordingly, fragments of the genetic information controlling the synthesis of xanthan also have utility in the commercial production of xanthan. The phrase "genetic information controlling the synthesis of xanthan" accordingly refers either to the original chromosomal DNA that controls xanthan synthesis as described above or fragments of this original chromosomal DNA containing one or more individual genes capable of controlling the synthesis of xanthan (e.g., individual genes encoding an enzyme utilized in xanthan synthesis).

After a Xanthomonas strain having a xanthan-increasing modification is cultured, xanthan is separated from the culture medium utilizing any technique capable of achieving this result such as the standard techniques already being utilized commercially. See, for example, Kennedy et al., supra. and Rogovin et al., supra. One simple technique involves filtering a liquid culture medium to remove growing bacterial cells, adding isopropyl alcohol to the filtrate to precipitate the exopolysaccharides, and collecting the precipitate on a filter followed by drying (optionally with heat and/or under a vaccuum).

The invention now being generally described, the same will be better understood by reference to the following detailed examples which are provided for purposes of illustration only and are not to be considered limiting of the invention unless so stated.

EXAMPLE 1

Use of Exogenous Genetic Information

Controlling the Synthesis of Xanthan

In summary, mutations that block the synthesis of xanthan gum by *Xanthomonas campestris* B1459 were isolated as nonmucoid colonies after treatment with ethylmethane sulfonate and used to identify DNA fragments containing xanthan genes. Complete libraries of DNA fragments from wild-type *X. campestris* were cloned into *E. coli* using a broad host range cosmid vector and then transferred into each mutant strain by conjugal mating. Cloned fragments that restored xanthan gum synthesis (Xgs$^+$; mucoidy) were characterized according to restriction pattern, DNA sequence homology and complementation of a subset of Xgs$^-$. Groups of clones that contained overlapping homologous DNA were found to complement specific Xgs$^-$ mutations. The results suggested a possible clustering of genetic loci involved in synthesis of xanthan. Other apparently unlinked loci were also discovered. Two forms of complementation were observed. In most instances, independently isolated cosmid clones that complemented a single mutation were found to be partially homologous. Less frequent was the second form of complementation, where two cosmid clones that lack any homologous sequences restored the mucoid phenotype to a single mutant. Restoration of the wild-type mucoid phenotype was shown, in the one case that was studied in detail, to coincide with homologous recombination between a normal cloned DNA residing on a plasmid and the mutant chromosomal locus. Lastly, the degree of restoration of xanthan synthesis was measured for the complemented mutants and for wild-type *X. campestris* carrying multiple copies of the cosmid clones. Details of experiment techniques and results are set forth below.

Materials and Methods

Bacterial strains and plasmids. *Xanthomonas campestris* B1459S-4L-II (our strain X55) obtained from the Northern Regional Research Center was the Xgs$^+$ (xanthan gum synthesis positive) parent of all our *X. campestris* strains. Strain X59 was a spontaneous rifampicin-resistant derivative of X55 that was also fully Xgs$^+$. Rif$^r$ derivatives of X55 arose at a frequencey of about $10^{-9}$ and were selected on agar plates containing Luria broth supplemented with rifampicin at 60 μ/ml. Bacteriophage λ b221 rex::Tn5 cI857 Oam29 Pam80 (Ruvkun et al., *Nature* (1981) 289:85–88) was the source of Tn5 for mapping by insertional gene inactivation. Strain LE392 was the permissive host for propagating the phage. All strains and plasmids are listed in Table 1.

TABLE 1

Bacterial Strains and Plasmids

| Name | Genotype or Phenotype[a] | Reference or Source |
|---|---|---|
| *X. campestris* | | |
| X55 | Xgs$^+$, prototroph | ATCC 13951 |
| X59 | Xgs$^+$, prototroph, Rif$^r$ | This Example |
| X59m1 | Xgs$^-$, prototroph, Rif$^r$ | This Example |
| X59m8 | Xgs$^-$, auxotroph, Rif$^r$ | This Example |
| X59m9 | Xgs$^-$, prototroph, Rif$^r$ | This Example |
| X59m11 | Xgs$^-$, auxotroph, Rif$^r$ | This Example |
| X59m31 | Xgs$^-$, prototroph, Rif$^r$ | This Example |
| X59m45 | Xgs$^-$, prototroph, Rif$^r$ | This Example |
| X59m48 | Xgs$^-$, auxotroph, Rif$^r$ | This Example |
| X59m65 | Xgs$^-$, prototroph, Rif$^r$ | This Example |
| X59m82 | Xgs$^-$, prototroph, Rif$^r$ | This Example |
| X59m96 | Xgs$^-$, auxotroph, Rif$^r$ | This Example |
| X59m145 | Xgs$^-$, prototroph, Rif$^r$ | This Example |
| *E. coli* | | |
| HB101 | F$^-$ hsd20 (r$_B^-$ m$_B^-$), recA13, ara-14, proA2, lacY1, galK2, rpsL20 (streptomycin-resistance), | Bethesda Research Labs |

TABLE 1-continued

Bacterial Strains and Plasmids

| Name | Genotype or Phenotype[a] | Reference or Source |
|---|---|---|
| JM109 | xyl-5, mtl-1, supE44, thi, leu, λ⁻ recA1, endA1, gyrA96, thi, hsdR17, supE44, relA1, Δ(lac-proAB), [F'traD36, proAB, lacI$^q$ZΔM15] | Bethesda Research Labs |
| LE392 | F⁻, hsdR514, ($r_k^- m_k^-$) supE44, supF58, λ⁻, galK2, galT22, metB1, trpR55, lacY1, Δlac IZY-6 | L. Enquist |
| Bacteriophage | λb221 rex::Tn5 (Kan$^r$) cI857, Oam29, Pam80 | Ruvkun et al. Nature (1981) 289:85–88 |
| Plasmids | | |
| pRK311 | RK2 origin, Tra⁺, Mob⁻, Tet$^r$, λcos, lacZ(∝) | Ditta et al. Plasmid (1985) 13:149–153 |
| pRK2013 | ColE1 origin, Imm⁺, Amp$^r$, Tra⁺, Mob⁺, Kan$^r$ | Figurski et al. ProcNatlAcadSciUSA (1979) 76:1648–1652 |
| pUC13 | Amp$^r$, ColE1 origin | Veira et al. Gene (1982) 19:259–268 |
| c1 | pRK3$^{11}$, Tet$^r$, complements m1 | This Example |
| c8 | pRK311, Tet$^r$, complements m8 | This Example |
| c8::Tn5-  1- → 20 | Tet$^r$, Kan$^r$ | This Example |
| c9 | pRK311, Tet$^r$, complements m9 | This Example |
| c31 | pRK311, Tet$^r$, complements m31 | This Example |
| c45 | PRK311, Tet$^r$ complements m45 | This Example |
| c65 | pRK311, Tet$^r$ complements m65 | This Example |
| c82 | pRK311, Tet$^r$ complements m82 | This Example |
| c1H5 | PRK311, Tet$^r$ complements m1 | This Example |
| c9H7 | PRK311, Tet$^r$ complements m9 | This Example |
| c9e | pRK311, Tet$^r$ complements m9 | This Example |

[a]Abbreviations: Xgs⁺, xanthan gum synthesis; Rif$^r$, rifampicin resistance; Tet$^r$, tetracycline resistance; Kan$^r$, kanamycin resistance; Amp$^r$, ampicillin resistance; Imm⁺, colicin E1 immunity; Tra and Mob, transfer and mobilization functions of RK2 plasmed.

Growth media. Xanthomonas species were cultured by shaking in liquid YT medium at 30° C. with rifampicin at 50 μ/ml, tetracycline at 7.5 μ/ml and/or kanamycin at 50 μg/ml added for plasmid maintenance. YT medium contains Bacto tryptone (16 g/l) Bacto yeast extract (10 g/l) and NaCl (5 g/l). All nutrient agar plates contained TBAB (tryptose blood agar base from Difco) plus starch at 1% (w/v). Selection plates for conjugal matings contained tetracycline at 7.5 μg/ml, kanamycin at 50 μg/ml and rifampicin at 50 μg/ml. Minimal agar plates contained M9 inorganic salts (Anderson, *Proc. Natl. Acad. Sci.* USA (1946) 32:120–128) plus glucose, mannose or fructose at 1% (w/v) as the carbon source. Liquid medium for shake flask experiments to measure xanthan accumulation was referred to as "XG004" and consisted of 1× basic salts, 0.5% (w/v) tryptone, 0.25% (w/v) yeast extract, 1× trace minerals, 0.01% (w/v) CaCl and 2% (w/v) glucose. 10× basic salts consists of 6.8 g $KH_2PO_4$, 0.2 g $MgSO_4.7H_2O$, 2.2 g L-glutamic acid, 2 g citric acid in 100 ml with pH adjusted to 7 with NaOH at 30° C. 1000× trace minerals was 2.25 g $FeCl_3.6 H_2O$, 1.41 g $MnSO_4.H_2O$, 2.2 g $ZnSO_4.7H_2O$, 0.25 g $CuSO_4.5H_2O$, 0.4 g $CoCl_2.6H_2O$, 0.26 g $Na_2MoO_4.2H_2O$, 0.4 g $H_3BO_3$ and 0.06 g KI per liter of deionized $H_2O$ (with HCl added to solubilize the salts). *E. Coli* was grown in Luria broth at 37° C. with tetracycline at 10 μ/ml and kanamycin at 50 μ/ml as appropriate or on agar plates containing Luria broth or TBAB (Difco).

*Mutagenesis of X. campestris.* About 2×10⁹ freshly grown cells (an absorbance at 600 nm of 1 equals 10⁹ *X. campestris* cells) were resuspended in 2 ml of minimal salts medium and shaken at 30° C. with 0 to 40 μl of ethylmethane sulfonate (EMS) for 1, 2 or 3 h. Samples of 0.5 ml were taken from each treatment, washed two times with YT medium and resuspended in 2 ml of YT medium and shaken overnight at 30° C. Dilutions were spread on TBAB plus 1% (w/v) starch plates. After three days, nonmucoid colonies (about 1% of the total) were saved. The mutants designated X59m1 to X59m150, were tested for retention of the Rif$^r$ marker of the parent X59, for the presence of cleared zones around colonies on plates containing starch and for ability to utilize different carbon sources.

DNA isolation and recombinant DNA techniques. Plasmid DNA was isolated by the boiling method of Birnboim and Doly (*Nucleic Acids Res.* (1979) 7:1513– 1523). Frequently used plasmids were further purified by equilibrium sedimentation in density gradients of CsCl containing ethidium bromide (Maniatis et al. 1982. Molecular Cloning, A Laboratory Manual. Cold Spring Harbor Laboratory, Cold Spring Harbor, N.Y.). Restriction enzymes (from Boehringer Mannheim, GmbH) were used according to the manufacturer's instructions. DNA sequence homology was demonstrated by the blotting method of Southern (Maniatis et al., supra) and used Zeta-probe (Bio-Rad) for DNA immobilization. DNA for use as a hybridization probe was labeled with [$^{32}$P]dCTP (using a nick translation reagent kit from Bethesda Research Laboratories). Fragments of DNA were separated by electrophoresis through agarose gels (0.6 to 0.7% w/v) in Tris-acetate buffer (Maniatis et al., supra).

Conjugation and complementation of Xgs$^-$ mutants. The complete library (or specific elements of the library) were transferred from *E. coli* to *X. campestris* by a triparental mating scheme (Ditta et al., *Proc. Natl. Acad. Sci.* USA (1980) 77:7347–7351. From fresh overnight cultures, $10^9$ recipient cells (*X. campestris* Xgs$^-$ mutants), $5 \times 10^8$ donor cells (JM109-L[X59], the library) and $5 \times 10^8$ helper cells (*E. coli* HB101 containing plasmid pRK2013) were mixed and passed through an HA 0.45 micron Millipore filter. The filters were incubated on TBAB plates overnight at 30° C. and then the cells were washed into 2 ml of selecting medium (TBAB plus tetracycline at 7.5 µg/ml and rifampicin at 50 µg/ml). The cells were diluted by $10^4$ to $10^5$ fold and spread on selection plates containing antibiotics. Complementation (restoration of the Xgs$^+$ phenotype in an Xgs$^-$ mutant) occurred at a frequency of 0.1 to 0.5%. The Xgs$^+$ exconjugants were purified and the recombinant plasmid was isolated and transferred back to *E. coli* JM109 for storage and further purification. Subsequent matings with a purified member of the library raised the Xgs$^+$ frequency in the exconjugants to 100%.

Measurement of xanthan accumulation. Strains to be tested were grown in liquid XG004 medium overnight, diluted, and resuspended at the same cell density. Flasks (125 ml capacity) containing 10 ml of medium XG004 were inoculated with equal numbers of cells ($1 \times 10^8$) and shaken at 28° C. at 250 rpm. At the time of sampling, 20 ml of isopropyl alcohol was added to each flask to precipitate the exopolysaccharides. The precipitate was collected on a GFA filter, which was then dried in a vacuum oven, and weighed.

Results

Isolation of mutants deficient in xanthan gum synthesis (Xgs$^-$). Strain X55 (NRRL B1459S-4L-II from the Northern Regional Research Center) is the "wild-type" parent of most xanthan-producing strains of *X. campestris* in use today. Strain X55 was the parent of all other *X. campestris* used in this work. A spontaneous Rif$^r$ derivative of X55 was isolated by spreading about $10^9$ bacteria on a plate containing rifampicin at 60 µg/ml. The Rif$^r$ phenotype of X59 was useful as a marker to distinguish progeny from contaminants following mutagenesis and as a counterselection for *E. coli* Rif$^s$ donors in conjugal matings. Both X55 and X59 form indistinguishable mucoid colonies on nutrient and minimal agar plates.

A collection of Xgs$^-$ mutants was generated by exposing strain X59 (and less frequently X55) to ethylmethane sulfonate (EMS). After growth at 30° C. for 3 d, nonmucoid colonies were selected and purified for further use. In most cases the nonmucoid colonies were distinctively different in appearance, but some independently isolated mutants displayed similar nonmucoid appearance. The latter could be distinguished by plating on different carbohydrate sources and as a function of time of growth. Only one mutant was selected from each treatment with EMS, unless colony morphology was clearly distinctive. Mutants of X59, serially designated X59m1 to X59m200, were tested for the parental Rif$^r$ marker. Other indications that a survivor of mutagenesis was *X. campestris*, an amylase producer, was the clear zone surrounding colonies spread on a nutrient agar plate containing starch and the characteristic yellowish pigment of the colony. Many of the mutants were also tested for their ability to grow on minimal agar plates containing various sugar substrates in order to distinguish unique isolates from siblings.

Cloning of *X. campestris* DNA into a cosmid vector. Total DNA from strain X59 (Xgs$^+$) was prepared by the boiling method of Birnboim and Doly, supra, and partially digested with Sau3A restriction endonuclease. Large fragments of 20 to 30 kb were purified by velocity sedimentation in neutral sucrose gradients. This ensured that only contiguous chromosomal DNA fragments were inserted in the cloning vector upon ligation. The cloning vector was the broad host range cosmid, pRK311, constructed by Ditta et al., supra. DNA fragments to be cloned were inserted into the BamHI sequence of the multiple cloning site within the lacZ portion of the vector. Using the in vitro packaging kit of Stratagene, we selected for insertions of DNA of about 20 to 25 kb into the cosmid vectors. The pRK311 vector also carries a selectable tetracycline-resistance gene. After in vitro ligation and packaging, *E. coli* JM109 was transfected with phage particles, and tetracycline-resistant colonies were individually saved. Each tetracycline-resistant colony contained the plasmid vector plus a 20 to 25 kb insertion of *X. campestris* DNA. A library of fragments of DNA resulted from pooling the clones. Since the number of clones in each library exceeded 1000 we were at least 99.9% certain of having all fragments of the *X. campestris* chromosome represented at least once. Three different libraries were used in this example.

Complementation of Xgs$^-$ defects by cloned normal DNA. Intergenic conjugal matings were used to transfer DNA. The RK2-derived pRK311 cosmid has a broad host range but is not self-transmissible. In order for pRK311 to be transferred by conjugation between *E. coli* and *X. campestris* a second "helper" plasmid was used, pRK2013, which has a limited host range that does not include *X. campestris*. Transfer of recombinant cosmids was accomplished by a triparental mating that included *E. coli* JM109/pRK311, JM109/pRK2013 and the recipient *X. campestris* Xgs$^-$ mutant.

About 15 different Xgs$^-$ mutants were complemented and restored to mucoidy (Xgs$^+$) by conjugal mating with the complete library of *X. campestris* genes. The frequency of complementation was about 0.1% for most matings, as would be expected if there was only one copy of each gene per chromosome. The results can be understood by considering a set of related colonies: X59-pRK311, X59m45-pRK311 and X59m45-c45. The presence of the c45 cosmid restores the mucoid appearance as seen for the wild-type X59. The mucoid phenotype for X59m45-c45 depended on the continued presence of the recombinant plasmid, as judged by the maintenance of the Tet$^r$ gene of the plasmid. A similar overall pattern was seen for all complemented Xgs$^-$ mutants. Several mucoid exconjugants were picked and purified by replating. DNA was prepared for each and transformed into *E. coli* and then mated back into the original mutant Xgs$^-$ mutant strain. In each case this resulted in 100% complementation and all of the tetracycline-resistant exconjugants carried the same recombinant cosmid. The transformants of E. coli also served as a source of DNA for restriction mapping and DNA hybridization tests by Southern blotting. A summary of the complementation data is included in Table 2.

TABLE 2

Complementation of Xgs⁻ Mutations by Wild-Type Cloned X. campestris DNA[a]

| Mutant | c1 | c8 | c9 | c11 | c31 | c45 | c65 | c82 |
|--------|----|----|----|-----|-----|-----|-----|-----|
| m1 | + | +/− | − | − | +/− | − | +/− | − |
| m8 | − | + | − | − | + | − | + | − |
| m9 | − | +/− | + | + | − | − | − | + |
| m11 | − | +/− | + | + | − | − | − | + |
| m31 | − | + | − | − | + | − | + | − |
| m45 | − | + | − | − | − | + | − | − |
| m48 | − | + | − | − | − | + | − | − |
| m65 | − | + | − | − | + | − | + | − |
| m82 | − | +/− | + | + | +/− | − | +/− | + |
| m96 | − | + | − | − | + | − | + | − |
| m145 | − | − | − | NT | − | − | − | + |

[a]Xgs⁻ mutants that received a recombinant cosmid by mating were scored for mucoid (+) or nonmucoid (−) appearance by visual inspection of colonies. A +/− designation indicates a partial mucoidy. NT; not tested.

Alignment of cloned inserts and Xgs⁻ mutations by restriction mapping, DNA hybridization and genetic complementation. When more than one recombinant plasmid from the complete library complemented the same mutation, we usually found that they were either indistinguishable sibling clones or shared considerable DNA homology. DNA hybridization analyses demonstrated this point. Several recombinant plasmids were digested with a mixture of EcoRI and HindIII enzymes. HindIII cleaves in the multiple-cloning-site to one side of the cloned insert and EcoRI cleaves to the other side and also within the vector. This produces two fragments of vector DNA of about 8 and 13 kbp. The digestion products were separated by electrophoresis through agarose gels and two samples (A and B) containing the same digestion products were analyzed. Most of the visible bands from ethidium bromide staining were X59 DNA. The hybridization probes for the A sample were radiolabeled c45 plasmid and for the B sample, the plasmid c31. The hybridization pattern indicated that cosmids c8, c31, c45 and c65 carry overlapping segments of chromosomal DNA. The region in common between these four clones includes restriction fragments of 0.6 and 1.2 kb and part of the 4.3 kb fragment.

Additional hybridization results were obtained from a separate but similar analysis. Plasmid DNA was purified, restricted with a mix of EcoRI and HindIII enzymes and fragments were separated by agarose gel electrophoresis and then transferred to filters. In a first sample the probe was radiolabeled c9H7 and in a second sample, c1H5. The hybridization pattern for the first sample showed homology between c9H7, c9 and c145, but not between c9H7 and c45-2, c45-1, c8, c31, c32b, c1 or c1H5. The pattern of the second sample showed that c1H5 is homologous only to c1. Cosmid c1H5 was initially selected from the library of cloned fragments because it hybridized to c1. The hybridization results were the basis for compiling the map shown as FIG. 1.

The deduced locations of Xgs⁻ mutations are shown in FIG. 1 above the map of EcoRI and HindIII restriction sites labeled "R/H" on the left. Mutants enclosed by braces have not been ordered with respect to each other. Overlapping cloned fragments could be aligned according to restriction pattern and DNA homology. Superimposed on this alignment are the results of complementation experiments with "+" signifying restoration of the Xgs⁺ phenotype to an Xgs⁻ mutant. The range of possible map positions for each mutant was then determined from the boundaries of each cloned fragment. Most of the mutants were distributed across a contiguous stretch of about 40 kbp, representing about 2% of the chromosome of X. campestris.

Two other unlinked loci involved in xanthan synthesis were also identified. One locus is represented by four overlapping cloned fragments carried on cosmids c9, c11, c9H7 and c82. All four restore the Xgs⁺ mucoid phenotype to the independent mutants m9, m11 and m82. Another pair of cosmids (c1 and c1H5) share homology with each other, but not with either of the other two sets.

Xanthan synthesis by exconjugants of X59 with multiple copies of complementing cloned genes. We transferred each complementing cloned by mating into X59, already Xgs⁺, and measured xanthan synthesis. For a control we used X59 bearing the vector alone, pRK311. The cells were grown in shake flasks at 30° C., starting from inocula of $10^7$ cells per ml. The amount of xanthan was determined by standard methods: precipitation of the exopolysaccharides by two volumes of isopropanol, drying and weighing. For most complementing clones the extra gene copies had no detectable effect or caused a decrease in xanthan yield. For those that accumulated amounts of xanthan significantly higher than the control, the xanthan and cell growth data are given in FIG. 2. In no case was the increase in accumulation greater than 20%. However, the rate of xanthan accumulation between 24 and 36 hours for X59c45 was twice that for the control X59-pRK311. When X59 without pRK311 was included in the time course experiments we found that the large vector plasmid itself had a negative effect on xanthan synthesis (data not shown). In a similar experiment X59-c8 produced an average of 22% more xanthan gum than its parent strain X59 (48-hr growth period).

This Example demonstrates that all of the three complementary regions described in FIG. 1 containing xanthan genes are useful in the preparation of strains showing increased xanthan production. Reproducible changes in xanthan accumulation were observed with the introduction of exogenous genetic information, but the magnitude of change was small, plus or minus about 15%. Suppression of xanthan production was caused by the large plasmid vector itself, which depressed cell growth and xanthan synthesis. Use of other plasmid vectors should improve strain productivity.

EXAMPLE 2

Drug-Resistance and Xanthan Synthesis

Two different mutant phenotypes were associated with elevated accumulation of xanthan gum by Xanthomonas campestris (strain B1459). Among a set of spontaneous rifampicin-resistant mutants of the above strain (designated "X55" in this collection: see Example 1 above), there is a subset that accumulates more xanthan gum in the growth medium. The rifampicin-resistant derivatives that show this unexpected phenotype were X59, X34, X37 and X44. As shown in Table 3, these strains accumulate more xanthan compared to the rifampicin-sensitive parent X55.

A second phenotype, bacitracin-resistance, is also associated with elevated xanthan synthesis. Strain X50 is a bacitracin-resistant derivative of the rifampicin-resistant X59. The double mutant accumulates more xanthan gum than either its parent X59 or X55.

TABLE 3

| | Amount of Isopropyl Alcohol-Precipitable Polysaccharide[+] | | | | | | | |
|---|---|---|---|---|---|---|---|---|
| | Experimental Number[++] | | | | | | | |
| Strain | 1 | 2 | 3 | 4 | 5 | 6 | 7 | 8 |
| X55 | 38 | 43 | 40 | 35 | 37 | 28 | 26 | — |
| X59 | 42 | 49 | 44 | 47 | 45 | 33 | 39 | — |
| X34 | 42 | 48 | 42 | 44 | — | — | — | — |
| X37 | 44 | 58 | 44 | 44 | — | — | — | — |
| X44 | — | — | — | — | — | 37 | 35 | — |
| X50 | — | — | — | — | — | 41 | 41 | 40 |

[+]Expressed as mg from 8 g culture. The polysaccharides were precipitated from 8 g of culture by adding 1 volume isopropyl alcohol and mixing. The precipitate was collected by filtration onto a paper filter and then dried and weighed.
[++]Harvest times: experiment (1) 72 hr; (2–8) 48 hr. Cultures were 20 ml in 250 ml triple-baffled Erlenmeyer flasks. The growth medium for experiment 1 and 2 was medium "11" and for experiments 3–8 it was YM plus glucose. Medium 11 includes per liter of tap water - 1 g $(NH_4)_2HPO_4$, 1 g $NaNO_3$, 1 g Amberex, 0.01 g $MgSO_4 \cdot 7H_2O$, 0.1 g $CaCl_2$, 20 g glucose and trace minerals. YM plus glucose includes per liter - 3 g yeast extract, 3 g malt extract, 5 g peptone and 20 g glucose.

The techniques utilized to obtain these resistant strains are described below.

Rifampicin.

At least $10^9$ bacteria of strain X55 were spread on plates (YM plus glucose) containing rifampicin at 50–100 µg/ml, usually 60 µg/ml. The cultures were incubated at 30° C. for 2–3 days. The colonies that appeared were inspected. Colonies that appeared mucoid (Xgs[+]) and resistant to rifampicin upon restreaking to purify the mutated derivative were tested for accumulation of xanthan as described in the legend to Table 3 above.

Bacitracin

To isolate bacitracin-resistance strains, either X55 or the rifampicin-resistant derivative X59 was utilized. The results given in this example are for X59. About $10^9$ bacteria of strain X59 were spread evenly on plates (YM plus glucose) and allowed to dry. Then a drop of a solution containing bacitracin at 1–5 µg/ml water was spotted on the center of the plate. After 1–2 days of growth at 30° C., a clear zone was present where the bacitracin was added. Just inside the boundary separating the no-growth region from the growth region were several small colonies that survived the antibiotic treatment. These were picked and restreaked on plates (YM plus glucose) containing bacitracin at a concentration of 0.5 mg/ml.

Derivative X50 was obtained from parent X59. Other bacitracin-resistant colonies were seen but were not xanthan producers; such non-mucoid colonies were not studied further.

X50 was deposited with the American Type Culture Collection located at 12301 Park Lawn Drive, Rockville, Md. 20852 on May 17, 1993 and given ATCC designation 55429. This deposit was pursuant to the Budapest Treaty on the International Recognition of the Deposit of Micro-Organisms for the purposes of patent procedure and all restrictions thereon will be irrevocably removed upon the granting of a patent thereon.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A biologically pure culture of a strain a *Xanthomonas campestris* having all the identifying characteristics of *Xanthomonas campestris* ATCC 55429.

2. The biologically pure culture of claim 1, wherein said strain is *Xanthomonas campestris* ATCC 55429.

\* \* \* \* \*